(12) United States Patent
Herrmann

(10) Patent No.: US 9,005,554 B1
(45) Date of Patent: Apr. 14, 2015

(54) FISCHER TROPSCH METHOD FOR OFFSHORE PRODUCTION RISERS OR OIL AND GAS WELLS

(71) Applicant: Robert P. Herrmann, Houston, TX (US)

(72) Inventor: Robert P. Herrmann, Houston, TX (US)

( * ) Notice: Subject to any disclaimer, the term of this patent is extended or adjusted under 35 U.S.C. 154(b) by 0 days.

(21) Appl. No.: 14/594,452

(22) Filed: Jan. 12, 2015

Related U.S. Application Data

(62) Division of application No. 13/839,825, filed on Mar. 15, 2013.

(60) Provisional application No. 61/660,709, filed on Jun. 16, 2012.

(51) Int. Cl.
*B01J 8/06* (2006.01)
*B01J 8/00* (2006.01)
*C10G 2/00* (2006.01)

(52) U.S. Cl.
CPC .. *B01J 8/008* (2013.01); *C10G 2/00* (2013.01)

(58) Field of Classification Search
CPC ............. C07C 1/04; C10G 2/00; C10G 2/32; C10G 2/33
USPC .................................. 518/705, 706; 422/651
See application file for complete search history.

(56) References Cited

U.S. PATENT DOCUMENTS

| | | | |
|---|---|---|---|
| 3,322,195 A | 5/1967 | Brown et al. ................... 166/38 |
| 3,464,885 A | 9/1969 | Land et al. ...................... 162/17 |
| 3,606,999 A | 9/1971 | Lawless ............................. 23/1 |
| 3,853,759 A | 12/1974 | Titmas ......................... 210/600 |
| 4,039,302 A | 8/1977 | Khera ........................... 518/712 |
| 4,272,383 A | 6/1981 | McGrew ....................... 210/741 |
| 4,706,751 A | 11/1987 | Gondonin ..................... 166/401 |
| 4,826,800 A | 5/1989 | McAteer ....................... 502/303 |
| 4,929,348 A | 5/1990 | Rice ............................. 210/109 |
| 4,937,052 A | 6/1990 | Takahashi et al. ............ 422/242 |
| 5,052,482 A | 10/1991 | Gondonin ....................... 166/50 |
| 5,345,005 A | 9/1994 | Thakur et al. ................ 568/885 |
| 5,527,975 A * | 6/1996 | Cosserat et al. .............. 570/248 |
| 5,811,365 A | 9/1998 | Barry ............................ 502/343 |
| 5,824,217 A | 10/1998 | Pearl et al. ................. 210/321.75 |
| 5,891,829 A | 4/1999 | Vallejos et al. ............... 507/202 |
| 5,945,458 A | 8/1999 | Barry ............................ 518/715 |
| 7,232,848 B2 * | 6/2007 | Mohedas et al. ............. 518/726 |
| 7,581,592 B1 | 9/2009 | Bush et al. .................... 166/302 |
| 7,582,269 B2 | 9/2009 | McGrew ....................... 422/606 |
| 7,909,097 B2 | 3/2011 | Ayasse ......................... 166/256 |
| 8,091,643 B2 | 1/2012 | Mango .......................... 166/309 |
| 2003/0088138 A1 * | 5/2003 | Mart et al. ..................... 585/734 |
| 2011/0266197 A1 * | 11/2011 | Pinho et al. ............... 208/120.05 |

FOREIGN PATENT DOCUMENTS

| | | |
|---|---|---|
| EP | 142887 | 5/1985 |
| EP | 127220 | 12/1985 |
| EP | 221598 | 5/1987 |
| EP | 261870 | 3/1988 |
| GB | 2125062 | 2/1984 |
| GB | 2130113 | 5/1984 |
| GB | 2146350 | 4/1985 |
| WO | WO/01/38269 | 5/2001 |
| WO | WO/03/090925 | 11/2003 |

OTHER PUBLICATIONS

International Preliminary Report on Patentability in International Application No. PCT/US2013/046045 dated Dec. 24, 2014.
International Seach Report and Written Opinion in International Application No. PCT/US2013/046045, mailed Nov. 1, 2013.

* cited by examiner

*Primary Examiner* — Sudhakar Katakam
(74) *Attorney, Agent, or Firm* — Norton Rose Fulbright US LLP

(57) ABSTRACT

A method and an apparatus is disclosed that uses a gas lift tubing arrangement to produce synthetic hydrocarbon related products. Using the Fischer Tropsch process as an example, the tubing is packed with a suitable catalyst and then hydrogen and carbon monoxide are injected into the top of the tubing in a fashion similar to a gas lift process. As the gases travel past the catalyst, synthetic hydrocarbons are formed and heat is rejected. The synthetic hydrocarbons and water flow out of the bottom of the tubing and travel up the annulus to the surface. In some embodiments, this process is carried out in a producing well or a in producing riser. In a producing well or a producing riser, the production from the well which flows up the annulus cools the synthetic hydrocarbon derived products. In additional and alternate embodiments, this process can be used in non-flowing wells.

21 Claims, 6 Drawing Sheets

FISCHER TROPSCH METHOD FOR OFFSHORE PRODUCTION RISERS OR OIL AND GAS WELLS

CROSS-REFERENCE TO RELATED APPLICATION

The present application is a divisional application of U.S. application Ser. No. 13/839,825, filed Mar. 15, 2013, which claims the benefit of U.S. Provisional Application 61/660,709 filed on Jun. 16, 2012, which is incorporated by reference in its entirety.

TECHNICAL FIELD

The present disclosure relates generally to the production of synthetic hydrocarbon derived products. More specifically, the present disclosure provides a method and an apparatus capable of producing synthetic hydrocarbon derived products using a gas lift apparatus equipped with a tubing comprising a catalyst.

BACKGROUND OF THE INVENTION

A process used for converting gas to liquid petroleum can be accomplished using a Fischer-Tropsch catalyst. Since the invention of the original process by Franz Fischer and Hans Tropsch, working at the Kaiser Wilhelm Institute in the 1920s, many refinements and adjustments have been made to this process. The term "Fischer-Tropsch" now applies to a wide variety of similar processes (Fischer-Tropsch synthesis or Fischer-Tropsch chemistry). Fischer and Tropsch filed a number of patents, e.g., U.S. Pat. No. 1,746,464, related to this process.

The Fischer-Tropsch process involves a series of chemical reactions that lead to a variety of hydrocarbons ($C_nH_{(2n+2)}$). Useful reactions give alkanes:

$$(2n+1)H_2 + nCO \rightarrow C_nH_{(2n+2)} + nH_2O \quad (1)$$

where the term "n" represents a positive integer. The formation of methane (n=1) is generally unwanted. Most of the alkanes produced tend to be straight-chain hydrocarbons, suitable for use as a diesel fuel. In addition to alkane formation, competing reactions give small amounts of alkenes, as well as alcohols and other oxygenated hydrocarbons.

Several reactions are employed to adjust the $H_2/CO$ ratio. Most important is the water gas shift reaction, which provides a source of hydrogen at the expense of carbon monoxide:

$$H_2O + CO \rightarrow H_2 + CO_2 \quad (2)$$

For Fischer-Tropsch plants that use methane as the feedstock, another important reaction is steam reforming, which converts the methane into CO and $H_2$:

$$H_2O + CH_4 \rightarrow CO + 3H_2 \quad (3)$$

The conversion of CO to alkanes involves hydrogenation of CO, the hydrogenolysis (cleavage with $H_2$) of C—O bonds, and the formation of C—C bonds. Such reactions are assumed to proceed via initial formation of surface-bound metal carbonyls. The CO ligand is speculated to undergo dissociation, possibly into oxide and carbide ligands. Other potential intermediates are various C-1 fragments including formyl (CHO), hydroxycarbene (HCOH), hydroxymethyl ($CH_2OH$), methyl ($CH_3$), methylene ($CH_2$), methylidyne (CH), and hydroxymethylidyne (COH). Furthermore, and critical to the production of liquid fuels, are reactions that form C—C bonds, such as migratory insertion. Many related stoichiometric reactions have been simulated on discrete metal clusters, but homogeneous Fischer-Tropsch catalysts are poorly developed and of little commercial importance.

Generally, the Fischer-Tropsch process is operated in the temperature range of 150-300° C. (302-572° F.). Higher temperatures usually lead to faster reactions and higher conversion rates, but also tend to favor methane production. For this reason, the temperature is usually maintained at the low to middle part of the range. Increasing the pressure leads to higher conversion rates and also favors formation of long-chained alkanes, both of which are desirable. Typical pressures range from one to twenty atmospheres. High pressure may reduce the reaction temperature which would make the Fischer-Tropsch process compatible with most oilfield operations.

A variety of synthesis-gas compositions can be used. For cobalt-based catalysts the optimal $H_2:CO$ ratio is around 1.8-2.1. Iron-based catalysts promote the water-gas-shift reaction. Accordingly, iron-based catalysts can tolerate lower ratios of $H_2:CO$. This reactivity can be important for synthesis gas derived from coal or biomass, which tend to have relatively low $H_2:CO$ ratios (<1).

In general the product distribution of hydrocarbons formed during the Fischer-Tropsch process follows an Anderson-Schulz-Flory distribution, which can be expressed as:

$$Wn/n = (1-\alpha)2\alpha n - 1 \quad (4)$$

Where Wn is the weight fraction of hydrocarbon molecules containing n carbon atoms. The term "α" represents the chain growth probability or the probability that a molecule will continue reacting to form a longer chain. In general, α is largely determined by the catalyst and the specific process conditions.

Examination of equation (4) reveals that methane will always be the largest single product so long as α is less than 0.5. However, by increasing value of α to about one, the total amount of methane formed can be minimized compared to the sum of all of the various long-chained products. Increasing α increases the formation of long-chained hydrocarbons. The very long-chained hydrocarbons are waxes, which are solid at room temperature. Therefore, for production of liquid transportation fuels it may be necessary to crack some of the Fischer-Tropsch products. In order to avoid this, some researchers have proposed using zeolites or other catalyst substrates with fixed sized pores that can restrict the formation of hydrocarbons longer than some characteristic size (usually n<10). This way they can drive the reaction so as to minimize methane formation without producing lots of long-chained hydrocarbons. Such efforts have met with only limited success.

A variety of catalysts can be used for the Fischer-Tropsch process, but the most common are the transition metals cobalt, iron, and ruthenium. Cobalt, nickel, iron, molybdenum, tungsten, thorium, ruthenium, rhenium and platinum are known to be catalytically active, either alone or in combination, in the conversion of synthesis gas into hydrocarbons and oxygenated derivatives thereof. Of the aforesaid metals, cobalt, nickel and iron have been studied most extensively. Nickel tends to favor methane formation ("methanation"). Generally, the metals are used in combination with a support material, of which the most common are alumina, silica and carbon.

Cobalt-based catalysts are highly active, although iron may be more suitable for low-hydrogen-content synthesis gases such as those derived from coal due to its promotion of the water-gas-shift reaction. In addition to the active metal, the catalysts typically contain a number of "promoters," including potassium and copper. Group 1 alkali metals, including potassium, are a poison for cobalt catalysts but are promoters for iron catalysts. Catalysts are supported on high-surface-area binders/supports such as silica, alumina, or zeolites. Cobalt catalysts are more active for Fischer-Tropsch synthesis when the feedstock is natural gas. Natural gas has a high hydrogen to carbon ratio, so the water-gas-shift is not needed for cobalt catalysts. Iron catalysts are preferred for lower quality feedstocks such as coal or biomass.

Unlike the other metals used for this process (Co, Ni, Ru), which remain in the metallic state during synthesis, iron catalysts tend to form a number of phases, including various oxides and carbides during the reaction. Control of these phase transformations can be important in maintaining catalytic activity and preventing breakdown of the catalyst particles.

Fischer-Tropsch catalysts are sensitive to poisoning by sulfur-containing compounds. The sensitivity of the catalyst to sulfur is greater for cobalt-based catalysts than for their iron counterparts.

Promoters also have an important influence on activity. Alkali metal oxides and copper are common promoters, but the formulation depends on the primary metal. Alkali oxides on cobalt catalysts generally cause activity to drop severely even with very low alkali loadings. $C_5^+$ and $CO_2$ selectivity increase while methane and $C_2$-$C_4$ selectivity decrease. In addition, the olefin to paraffin ratio increases.

The use of cobalt as a catalytically active metal in combination with a support has been described in, for example, EP-A-127220, EP-A-142887, GB-A-2146350, GB-A-2130113 and GB-A-2125062. EP-A-127220, for example discloses the use of a catalyst comprising (i) 3-60 pbw cobalt, (ii) 0.1-100 pbw zirconium, titanium, ruthenium or chromium, per 100 pbw silica, alumina or silica-alumina, (iii) the catalyst having been prepared by kneading and/or impregnation.

EP 261870 describes a composition for use after reductive activation as a catalyst for the conversion of synthesis gas to hydrocarbons comprising as essential components (i) cobalt either as the elemental metal, oxide or a compound thermally decomposable to the elemental metal or oxide and (ii) zinc in the form of the oxide or a compound thermally decomposable to the oxide. The resultant catalysts, in contrast to many prior art cobalt-containing catalysts, are more selective to hydrocarbons in the C5-C120 range and can be very selective to a waxy hydrocarbon product. These catalysts may also contain in elemental form or oxide form one or more of the following metals as promoters: chromium, nickel, iron, molybdenum, tungsten, zirconium, gallium, thorium, lanthanum, cerium, ruthenium, rhenium, palladium or platinum suitably in amount up to 15% w/w. Exemplified compositions included chromium, zirconium, gallium and ruthenium as promoters.

U.S. Pat. No. 4,039,302 describes a catalyst containing cobalt oxide and zinc oxide for use in the synthesis of C1-C3 aliphatic hydrocarbons U.S. Pat. No. 4,826,800 describes a process for preparing a catalyst comprising cobalt and zinc oxide for use after reductive activation as a catalyst in the conversion of synthesis gas to hydrocarbons. The catalyst is prepared by mixing a solution, of a soluble zinc salt and a soluble cobalt salt with a precipitant such as ammonium hydroxide or ammonium carbonate and recovering the precipitate. The ratio of carbonate to metal is high in the described method, which has been found detrimental to the strength of the catalyst.

U.S. Pat. No. 5,345,005 relates to a Cu—Zn catalyst on alumina for the preparation of alcohols by hydrogenation of e.g. a ketone. In a comparative example, the preparation of a Cu—Zn—Co catalyst on alumina is described, wherein use is made of soda ash. However, the use of soda ash is found to be potentially detrimental to the strength of the catalyst. The particle size distribution range within which 90% of the volume of the Cu—Zn—Co catalyst described in U.S. Pat. No. 5,345,005 lies, is not specified. It is however expected that the use of soda ash in the preparation of the catalyst leads to a broadening in the particle size distribution.

U.S. Pat. No. 5,945,458 and U.S. Pat. No. 5,811,365 describe a Fischer-Tropsch process in the presence of a catalyst composition of a group VIII metal, e.g. cobalt, on a zinc oxide support. Such a catalyst is made by first preparing the support by adding a solution of zinc salt and other constituents to an alkaline bicarbonate solution. Next, the precipitate is separated from the bicarbonate solution by filtration to form a filter cake, which can thereafter be dried, calcined and loaded with the group VIII metal. The catalyst material is then formed into tablets, which tablets are crushed to form particles with a size of 250-500 µm, that can be used in a Fischer-Tropsch process. Additional post-treatments such as crushing, are required in order to obtain a catalyst powder with good strength properties. However, the obtained average particle size; as indicated above, is still relatively large. Moreover, crushing results in a broad particle size distribution and catalysts with such a large particle size and a broad particle size distribution tend to be less suitable for processes involving a bubble column, a slurry phase reactor or a loop reactor.

WO-A-01/38269 describes a three-phase system for carrying out a Fischer-Tropsch process wherein a catalyst suspension in a liquid medium is mixed with, gaseous reactants in a high shear mixing zone, after which the mixture is discharged in a post mixing zone. Thus mass transfer is said to be enhanced. As suitable catalysts inter alia cobalt catalysts on an inorganic support, such as zinc oxide are mentioned. The surface area of the support used for the preparation of these known catalysts is less than 100 g/m². These prior art cobalt based catalysts can be prepared by depositing cobalt on a suitable support, such as a zinc oxide support, by impregnation methodology. Other conventional preparation methods include precipitation routes, which typically involve crushing of a hard filter cake of catalyst material, resulting from the catalyst preparation process, into small particles.

WO 03/090925 describes a Fischer-Tropsch catalyst comprising particles of a cobalt and zinc co-precipitate having specific volume average particle size and particle size distributions. The catalysts essentially consist of cobalt and zinc oxide but may also contain other components commonly employed in Fischer-Tropsch catalysts such as ruthenium, hafnium, platinum, zirconium, palladium, rhenium, cerium, lanthanum, or a combination thereof. When present such promoters are typically used in a cobalt to promoter atomic ratio of up to 10:1.

EP 221598 describes supported catalysts comprising a metal component of iron, nickel or cobalt promoted by zirconium and in addition a noble metal from Group VIII of the Periodic Table. The catalysts are suitable for the preparation of hydrocarbons from carbon monoxide and hydrogen. Preferred noble metals include platinum or palladium and the catalysts are most suitably supported on silica or alumina.

Fischer-Tropsch plants associated with coal or related solid feedstocks (sources of carbon) must first convert the solid fuel into gaseous reactants, i.e. CO, $H_2$, and alkanes. This conversion is called gasification. Synthesis gas obtained from coal gasification tends to have a $H_2$/CO ratio of about 0.7 compared to the ideal ratio of about 2. This ratio is adjusted via the water-gas shift reaction. Coal-based Fischer-Tropsch plants can produce varying amounts of $CO_2$, depending upon the energy source of the gasification process. However, most coal-based plants rely on the feed coal to supply all the energy requirements of the Fischer-Tropsch process.

In summary, the Fischer-Tropsch process is performed by forcing hydrogen and carbon monoxide over a catalyst. The gases recombine into water and a petroleum product which can range between diesel and paraffin. Heat and water are also generated in this process. Currently, there is a need to improve the efficiency of this process. The present disclosure presents a method and an apparatus that improves the efficiency of catalytic processes.

BRIEF SUMMARY OF THE INVENTION

In general, the present disclosure provides a method and an apparatus that uses a gas lift tubing arrangement to produce synthetic hydrocarbons. In some embodiments, this method and apparatus uses a Fischer-Tropsch process to produce synthetic hydrocarbons. In the gas lift tubing arrangement, the tubing is packed and/or coated with a suitable catalyst and then hydrogen and carbon monoxide are injected into the top of the tubing in a fashion similar to a gas lift process. As the gases travel past the catalyst, synthetic hydrocarbons are formed and heat is rejected. The synthetic hydrocarbons and fluid flow out of the bottom of the tubing and travel up the annulus to the surface. Also, any gas not converted to synthetic hydrocarbons travels up annulus to the surface where it is reprocessed and re-injected. In some embodiments, this process is carried out in a producing well or a in producing riser. In a producing well or a producing riser, the production from the well which flows up the annulus cools the synthetic hydrocarbons. In additional and alternate embodiments, this process can be used in non-flowing wells. In this case cooling fluid is circulated up the annulus where it mixes with the newly formed petroleum product, and at the surface, the fluid is separated and cooled for re-injection.

In additional embodiments, the outside of the tubing is coated with a reverse water shift catalyst which converts $CO_2$ in the production stream to $CO$ and $H_2O$. In some embodiments, the catalyst or the concentration of the catalyst is distributed along length the tubing to control the conversion rate or product yield along the tubing. In specific examples, the catalyst is distributed or segregated along the tubing such that different heavy components of the gas stream (C2-C6) are converted into liquids which may be mixed with crude oil.

In alternate embodiments, more than one type of catalyst may be distributed along the length of the tubing. In some embodiments, the catalyst is distributed along the tubing in a plurality of segregated zones. This apparatus and method can be used to convert a first feedstock into a final product using a plurality of catalyst distributed along the tubing in a plurality of zones. For example, a first feedstock is converted into a first product using a first catalyst in the first zone. The first product from the first zone then becomes the second feedstock for the second zone, and in the second zone, the second feedstock is converted into a second product by a second catalyst. This process can be carried out over a plurality of zones to produce a final product.

In additional embodiments, the interaction between the catalyst and the feedstock produces an exothermic reaction. In this situation, the gas lift arrangement is configured such that the energy produced from this exothermic reaction is used to inhibit hydrate formation in the annulus where production is flowing (oil, gas, or both).

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

In oil wells and deepwater production risers, gas is sometimes injected through a tube running to or near the bottom of the well or riser to lift production fluid to the surface. This process is called gas lift and the equipment for doing this is in common use. In general, a gas lift apparatus is made of at least a gas lift tube and an annulus. The length of the tube (the gas lift string) varies but is typically 3,000 feet to 5,000 feet in length and made from 1" to 3.5" pipe.

Gas lift is one of a number of processes used to artificially lift oil or water from wells where there is insufficient reservoir pressure to produce the well. The normal gas lift process involves injecting gas through a tubing and returning up an annulus. The annulus of an oil well refers to any void between any piping, tubing or casing and the piping, tubing, or casing immediately surrounding it.

Injected gas aerates the fluid to reduce its density; the formation pressure is then sufficient to lift the oil column and force the fluid out of the wellbore. Gas may be injected continuously or intermittently, depending on the producing characteristics of the well and the arrangement of the gas-lift equipment.

The amount of injected gas needed to maximize oil production varies based on well conditions and geometries. Too much or too little injected gas will result in less than maximum production. Generally, the optimal amount of injected gas is determined by well tests, where the rate of injection is varied and liquid production (oil and perhaps water) is measured.

Although the gas is recovered from the oil at a later separation stage, the process requires energy to drive a compressor in order to raise the pressure of the gas to a level where it can be re-injected.

Figure 3:
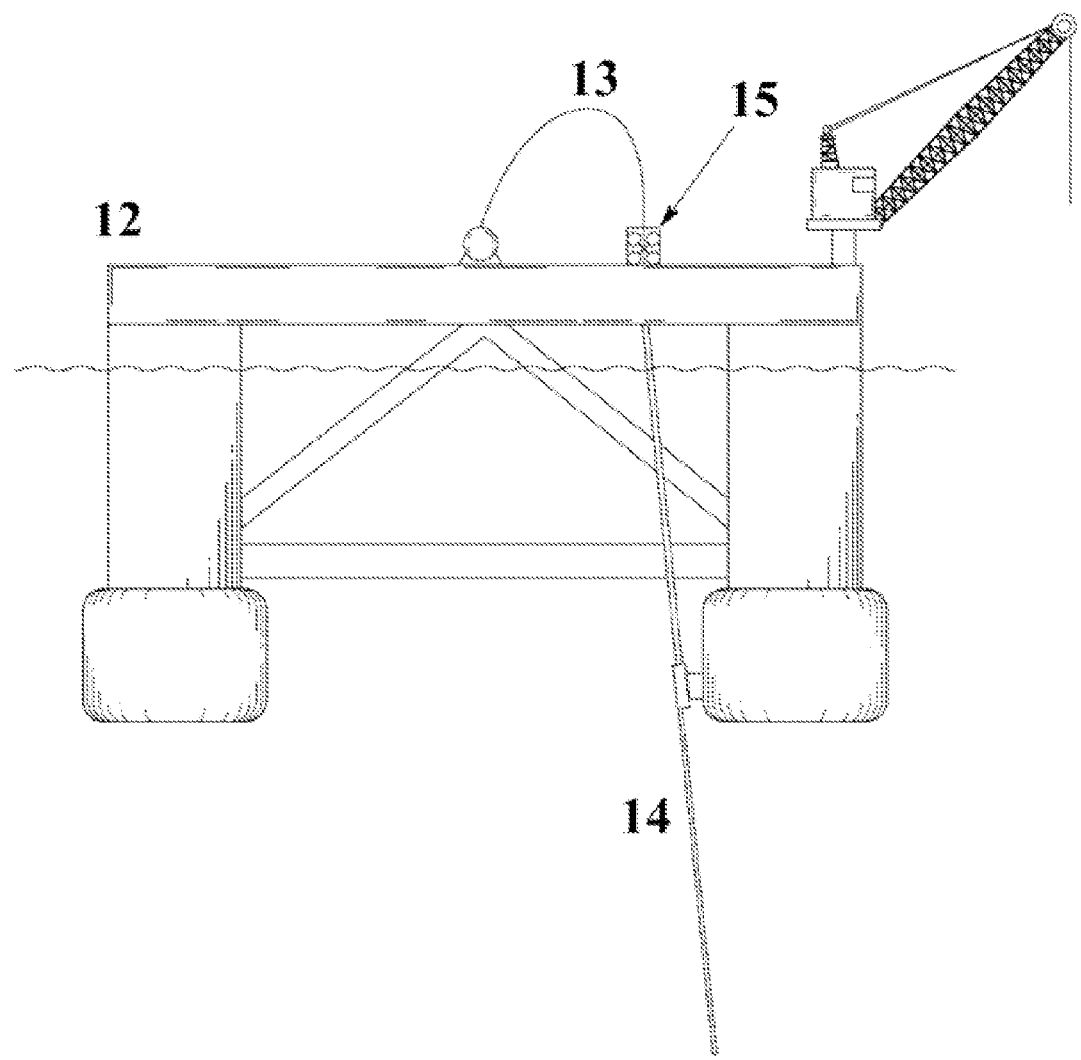
FIG. 3 provides an example of a coil tubing rig installing the gas lift tubing in a marine riser.

A coil-tubing rig 12 may be located on a production facility in a field in 7000 feet of water where production arrives via five separate steel catenary risers (SCR), with 8.5" inner diameter. The coil-tubing rig may be used for deploying a gas lift string 13 inside the marine production risers 14. FIG. 3 provides an example of a coil tubing rig 12.

Figure 4:
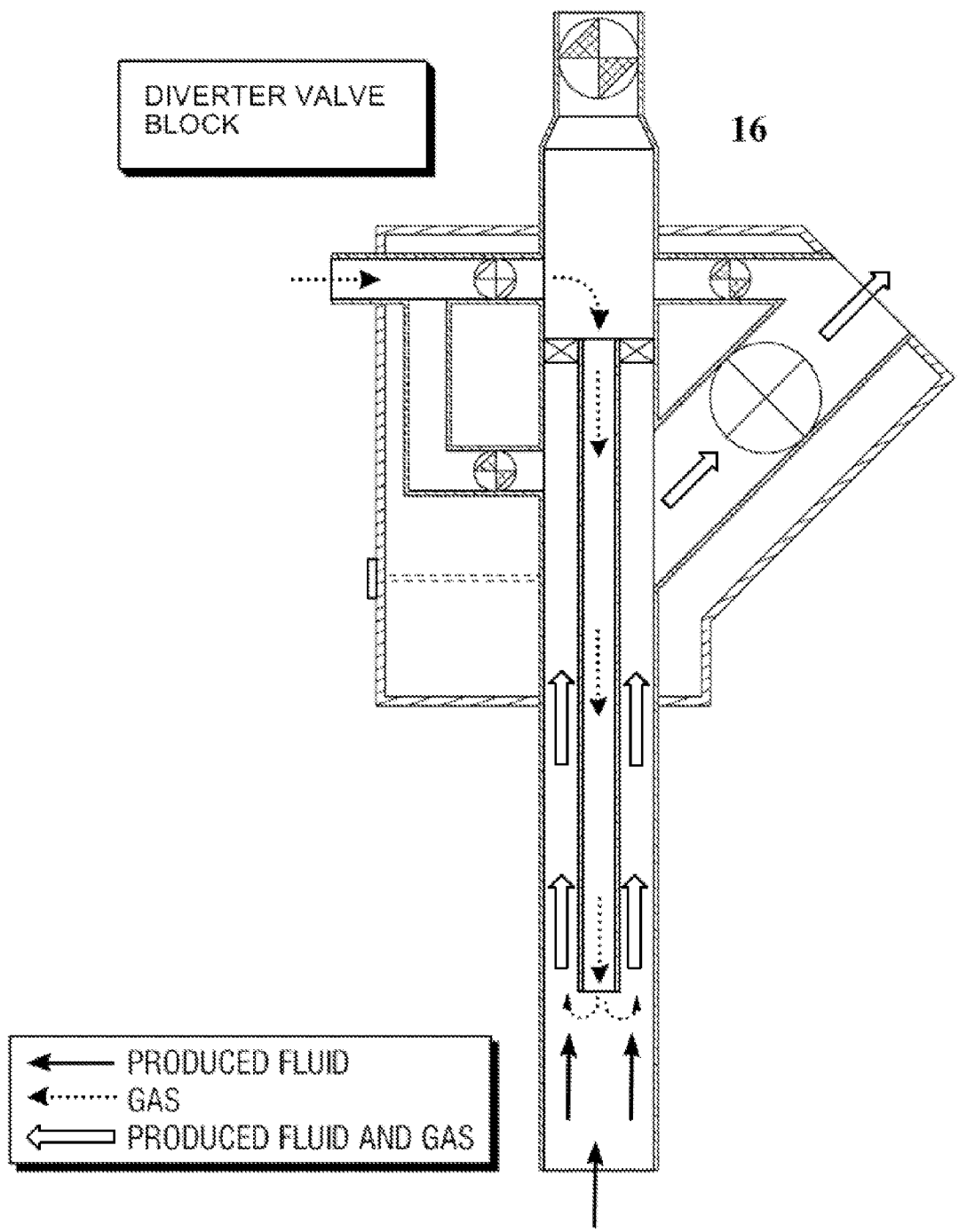
FIG. 4 shows an example of a gas lifting process through a gas lift string diverter valve.

A common use of a coil-tubing rig 12 is to deploy a gas lift string inside the marine riser 14, about 8,000 feet measured depth (MD). The coil tubing size ranges from 2⅜" to 3½" and handles up to 30 million or more standard cubic feet per day (mmscfd) of lift gas. A typical injection pressure is 2,500 pounds per square inch (psi). The coil tubing 13 is deployed by an injector 15 through a BOP which is nippled up to a diverter valve similar to that shown in FIG. 4.

Figure 5A:
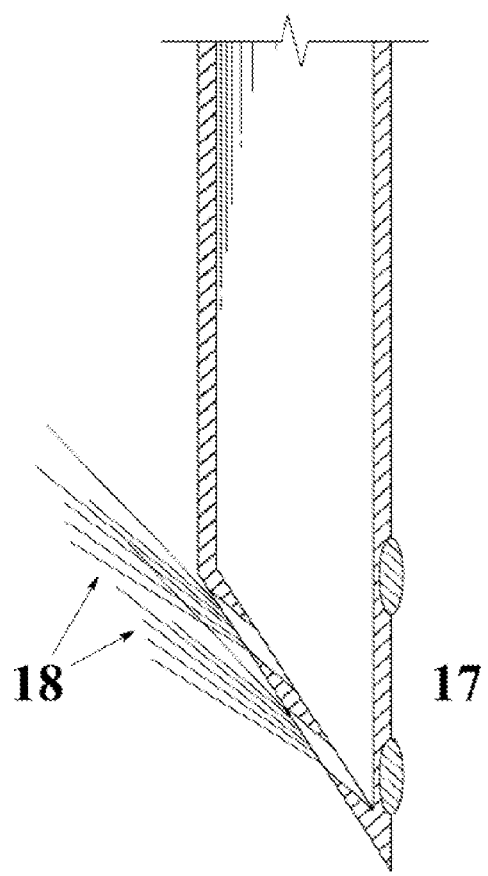
FIG. 5A shows side view of the nozzle on the gas lift string.
Figure 5B:
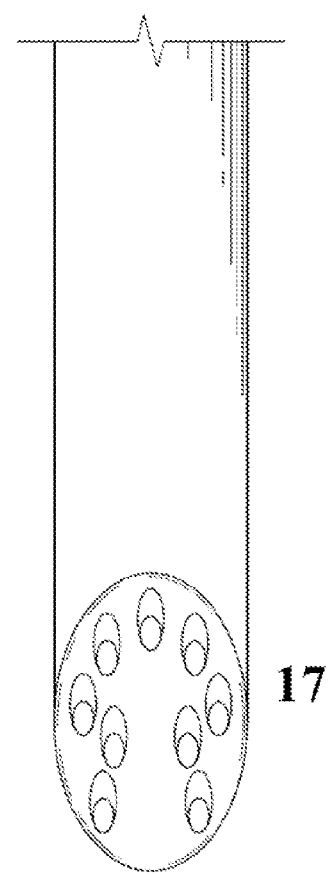
FIG. 5B shows a plane view the nozzle on the gas lift string.

A simple coil tubing gas lift string is often employed with no gas lift valves. FIGS. 5A and 5B show the nozzle on the inner string. In some embodiments, the jetting sub may be used to reduce vibration and provide effective mixing of the fluid. The shape of the sub and direction of the jet pin the bottom of the string against the riser. In some embodiments a jointed gas lift string utilized instead one conveyed by a coil-tubing rig.

The lift gas is often injected using export compressors which can deliver gas at 2,500 psi. In some embodiments a dedicated compressor is used to deliver lift gas.

Once rigged up a coil-tubing rig can deploy or pull a gas lift string within one day.

Figure 6:
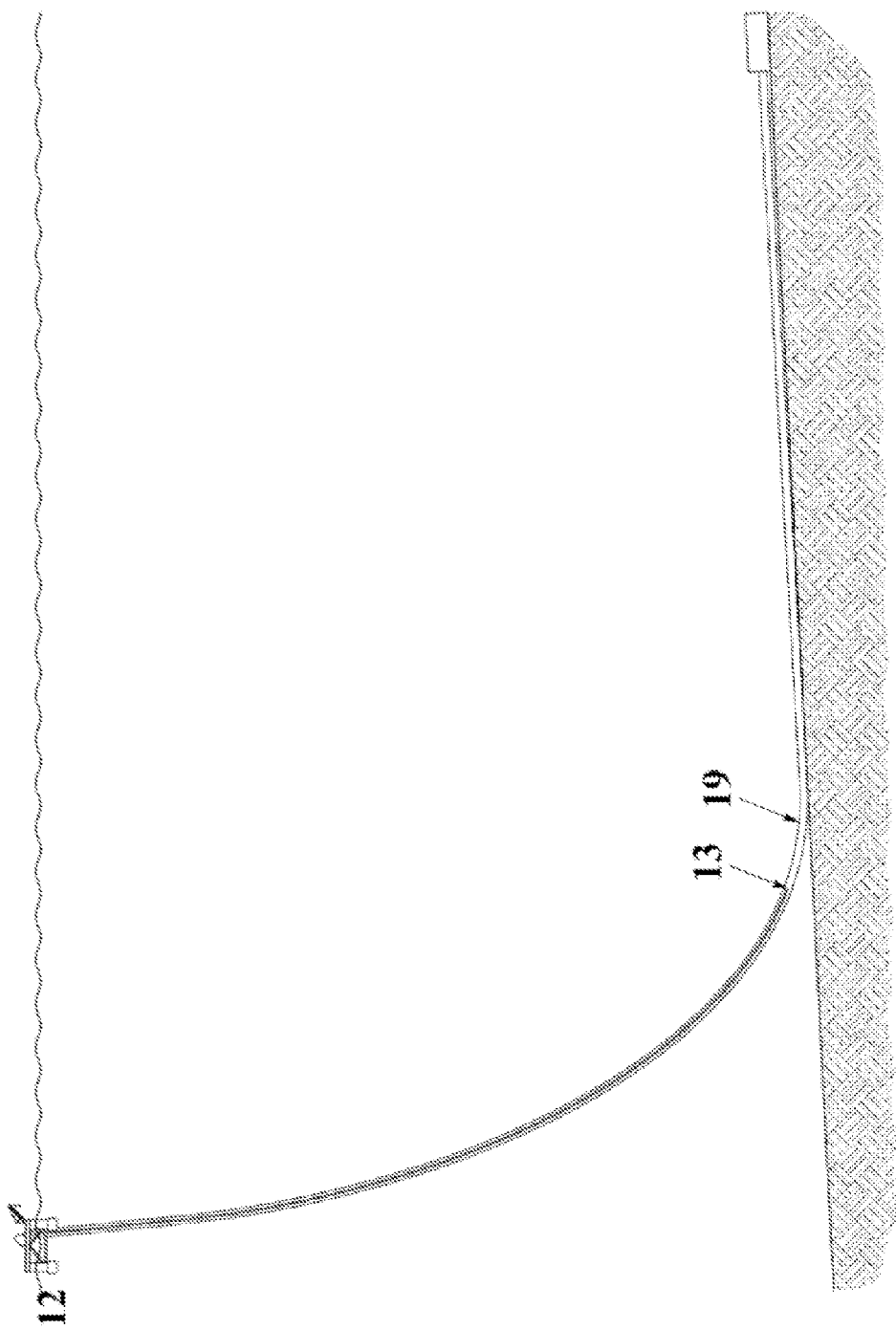
FIG. 6 shows an example of a gas lift string placed in a riser/flowline.

A typical steel catenary riser in 7,000 ft will have a 12 degree top angle and the length of the suspended riser is 8,800 ft. For example, FIG. 6 shows an example of a gas lift string 13 placed in a riser/flowline 19 having catenary curvature. Some embodiments use a flexible hose riser or a steel or flexible riser outfitted with buoyancy to create a second catenary curve (sometimes called a lazy-wave riser.

A tubing hanger is often run at the top of the gas lift string. The hanger is hung off in a valve block which seals the lower section of the valve block from the upper section. Lift gas is injected with pressure in the upper section where it enters the gas lift string. The lift gas exits at the bottom of the gas lift string where it mixes with the production in the annulus. The mixture returns up the annulus to the lower section of the valve block where it exits to the production facility. This valve block is often called a diverter valve.

Figure 7:
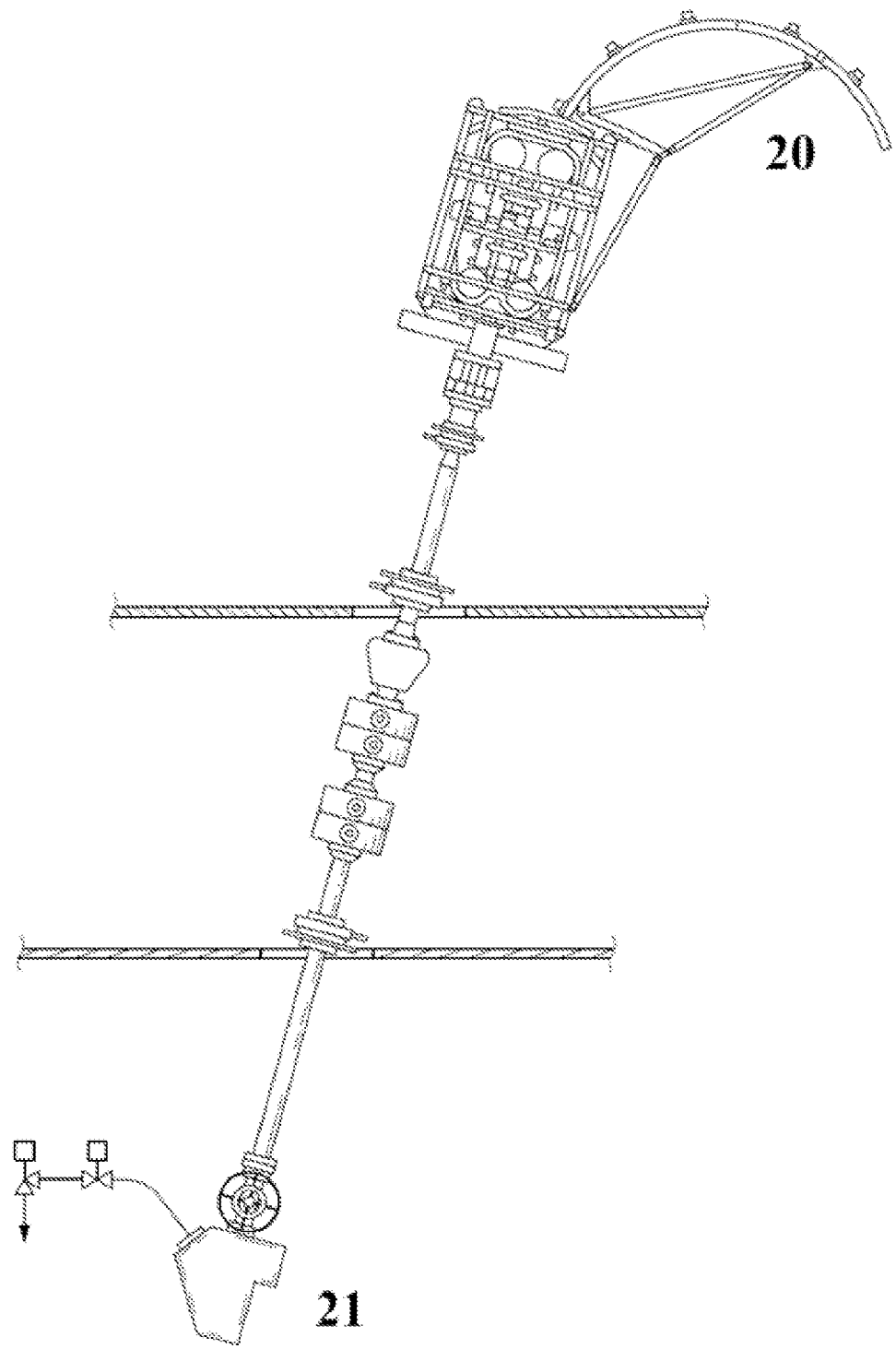
FIG. 7 shows the arrangement of the gas lift installation apparatus between the injector and the diverter.

FIG. 7 shows the arrangement of the gas lift apparatus between the coil-tubing rig injector and the diverter valve block 16 & 21. As shown in FIG. 7, the injector is connected to the diverter valve via a BOP stack. This arrangement is for installing a coil tubing gas lift string. Another embodiment uses a jointed gas lift string and is installed with a different type rig.

The present invention modifies this process. The modified process takes advantage of a gas lift tubing that is packed with a catalyst and/or coated with a catalyst. In specific embodiments, the gas lift tubing is packed with a Fischer-Tropsch catalyst. In other embodiments, the tubing is coated with a Fischer-Tropsch catalyst. Any Fischer-Tropsch catalyst suitable for the conversion of synthesis gas or $H_2$ and CO into hydrocarbons by the Fischer-Tropsch process may be used in the gas lift tubing arrangement described herein.

This modified process provides several advantages and provides solutions for several industry-wide problems. For example, this apparatus and process takes advantage of the fact that the catalyst deposited inside the tubing makes it easier to change and remove the catalyst by simply removing the tubing. Also, the process may be modified to transform a second feedstock into a particular product by simply removing the tubing containing a first catalyst and inserting a second tubing that has a second catalyst which is a different catalyst from the first catalyst. This demonstrates the ease in which the coil tubing can be replaced as well as the ease in which the catalyst and/or process can be changed. The arrangement also allows for the chemical reaction to take place at a much higher pressure. In normal reactors the maximum pressure is around 150 psi. However by using a modified gas lift string the reaction pressure can be raised to 10,000 psi or more with standard oilfield equipment. The higher pressure increases the efficiency of the chemical reaction whenever the reaction results in fewer molecules (as in the Fischer Tropsch process). This is called the Le Chatelier Principle. The higher pressure should also lower the reaction temperature.

In particular, the BOP is used in running the gas lift string (or tubing). Once the gas lift string is in place, the BOP is removed. The diverter valve consists of a multivalve block with an internal receptacle that allows a tubing hanger to be set. The hanger seals the annulus of the block and supports the tubing. Below this seal is an outlet valve through which the mixed production (the products) and the injection gas (the feedstock) exits the valve block. Gas is injected in the top of the hanger and the seal forces the gas to exit at the bottom of the gas lift string (the tubing).

In this process, hydrogen and carbon monoxide are injected into the top of the tubing packed with a suitable Fischer-Tropsch catalyst. Also, gas is injected through the tubing and the synthetic hydrocarbons flow out of the bottom of the tubing and travel up the annulus to the surface. As the gases ($H_2$ and CO) travel past the catalyst, synthetic hydrocarbons are formed and heat is produced. In some embodiments, the process is controlled by using cooling water or cooling oil. As the synthetic hydrocarbons and water flow out of the bottom of the tubing and travel up the annulus to the surface, any gas ($H_2$ and CO) not converted to synthetic hydrocarbons travels up annulus to the surface where it is reprocessed and re-injected through the tubing.

In some embodiments, this process is carried out in a producing well or in a producing riser. In a producing well or a producing marine riser, the production from the well which flows up the annulus cools the synthetic hydrocarbons. In additional and alternate embodiments, this process can be used in non-flowing wells. In this case cooling water or cooling oil is circulated up the annulus where it mixes with the newly formed petroleum product, and at the surface, the water is separated and cooled for re-injection.

The tubing can be adapted to carry out other processes in addition to the Fischer-Tropsch process. For example, these processes include, but are not limited to, the Haber process, the Haber-Bosch process, processes used to industrially produce ammonia or synthesis gas, the Claus process, the gas desulfurizing process, processes used to recover elemental sulfur from gaseous hydrogen sulfide, the Bergius Process, processes used to produce liquid hydrocarbons for use as synthetic fuel by hydrogenation of high-volatile bituminous coal at high temperature and pressure, the Deacon process, the Deacon-Leblanc process, the Sabatier process, the Sabatier-Senderens process, hydrogenation processes, oxidation processes, ammonia oxidation processes, the Andrussov synthesis, hydrocracking processes, alkylation processes, hydrotreating processes, catalytic reforming processes, coke formation, naphtha reforming processes, processes for the formation, reformation and functionalization of aromatics, cyclar processes, M2-forming process, catalytic dewaxing processes, isomerization processes, isopropyl alcohol formation, acetone formation, bisphenol-A formation, cumene formation, vinyl chloride formation, oxychlorination processes, formation of synthetic rubber from butadiene and styrene, formation of butadiene from butane or butenes, styrene production, nylon production, production of nylon intermediates, formation of adipic acid, formation of hexamethylenediamine, formation of nylon polymer, the Snia-Viscosa process, hydroformylation and carbonylation processes, metathesis of olefins, the Shell Higher-Olefins process, polyethylene formation, polypropylene formation, formation of ammonia synthesis gas, feedstock purification processes, hydrodesulfurization processes, processes for chlorine removal, sulfur adsorption, steam reforming, carbon monoxide removal, carbon monoxide conversion, and methanation, formation of methanol synthesis gas, formation of OXO synthesis gas, hydrogen production, processes for steam reforming of reducing gas, town gas production, autothermal reforming processes, the Claude Process, and processes for volatile organic compound removal. These exemplary processes are well known and it is within the skill of the ordinary artisan to be able to select the appropriate feedstock and catalyst needed to carry out any of these processes. The apparatus and method as described herein can be modified to carry out each of the aforementioned processes. These processes are well known by the skilled artisan. The appropriate feedstock, catalyst and resulting products are described for each of these processes in Lawrie Lloyd's Handbook of Industrial Catalyst (Springer 2011), which is incorporated herein by reference in its entirety.

In particular, the apparatus and methods disclosed herein are capable of carrying out the Fischer-Tropsch process, dry carbon dioxide ($CO_2$) reforming, hydrocarbon cracking of hydrocarbons, and/or steam reforming.

Carbon Dioxide Reforming

Carbon dioxide ($CO_2$) reforming (also known as dry reforming) is a method of producing synthesis gas (mixtures of hydrogen and carbon monoxide) from the reaction of carbon dioxide with hydrocarbons such as methane. Synthesis gas is conventionally produced via the steam reforming reaction. The methane carbon dioxide reforming reaction may be represented by:

$$CO_2 + CH_4 \rightarrow 2H_2 + 2CO \qquad (5)$$

In some embodiments, the gas lift tubing contains a catalyst suitable for carbon dioxide reforming. In this embodiment, carbon dioxide and methane (or other hydrocarbons) is the feedstock and the hydrogen and carbon monoxide are the products of this process.

Hydrocarbon Cracking

Cracking is the process whereby complex organic molecules such as kerogens or heavy hydrocarbons are broken down into simpler molecules such as light hydrocarbons, by the breaking of carbon-carbon bonds in the precursors. The rate of cracking and the end products are strongly dependent on the temperature and presence of catalysts. Cracking is the breakdown of a large alkane into smaller, more useful alkanes and alkenes. Simply put, hydrocarbon cracking is the process of breaking long-chain hydrocarbons into short ones.

Here is an example of cracking of butane $CH_3$—$CH_2$—$CH_2$—$CH_3$

The first possible mechanism is responsible for an estimated 48% of butane cracking products where breaking is done on the $CH_3$—$CH_2$ bond which results in the following radical products: $CH_3 \cdot$ and $\cdot CH_2$—$CH_2$—$CH_3$. After a certain number of steps, an alkane and an alkene are obtained: $CH_4 + CH_2 \!\!=\!\! CH$—$CH_3$.

The second possible mechanism is responsible for an estimated 38% of butane cracking products where breaking is done on the $CH_2$—$CH_2$ bond which results in the following radical products: $CH_3$—$CH_2 \cdot$ and $\cdot CH_2$—$CH_3$. After a certain number of steps, an alkane and an alkene are obtained: $CH_3$—$CH_3 + CH_2 \!\!=\!\! CH_2$ The third possible mechanism is responsible for an estimated 14% of butane cracking products where the C—H bond is broken. After a certain number of steps, an alkene and hydrogen gas is obtained: $CH_2 \!\!=\!\! CH$—$CH_2$—$CH_3 + H_2$ this is very useful since the catalyst is not exhausted and can be used for further cracking of hydrocarbons.

The catalytic cracking process involves the presence of acid catalysts (usually solid acids such as silica-alumina and zeolites) which promote a heterolytic (asymmetric) breakage of bonds yielding pairs of ions of opposite charges, usually a carbocation and the very unstable hydride anion. Carbon-localized free radicals and cations are both highly unstable and undergo processes of chain rearrangement, C—C scission in position beta as in cracking, and intra- and intermolecular hydrogen transfer or hydride transfer. In both types of processes, the corresponding reactive intermediates (radicals, ions) are permanently regenerated, and thus they proceed by a self-propagating chain mechanism. The chain of reactions is eventually terminated by radical or ion recombination.

In some embodiments, the gas lift tubing contains a catalyst suitable for hydrocarbon cracking. In this embodiment, a hydrocarbon (i.e. a hydrocarbon containing a range of carbons between 2 and 45 carbons, and/or any other range or specific number found between 2 and 45) is the feedstock and an alkane, alkene and/or hydrogen are the products of this process.

Steam Reforming

Steam reforming of natural gas or synthetic gas sometimes referred to as steam methane reforming (SMR) is the most common method of producing commercial bulk hydrogen as well as the hydrogen used in the industrial synthesis of ammonia. At high temperatures (700-1100° C.) and in the presence of a metal-based catalyst (nickel), steam reacts with methane to yield carbon monoxide and hydrogen. These two reactions are reversible in nature.

$$CH_4 + H_2O \leftrightarrows CO + 3H_2 \qquad (6)$$

Additional hydrogen can be recovered by a lower-temperature gas-shift reaction with the carbon monoxide produced. The reaction is summarized by:

$$CO + H_2O \rightarrow CO_2 + H_2 \qquad (7)$$

The first reaction is strongly endothermic (consumes heat), the second reaction is mildly exothermic (produces heat).

In some embodiments, the gas lift tubing contains a catalyst suitable for steam reforming. In this embodiment, methane and water are the feedstock and an carbon monoxide and hydrogen are the products of first stage of this process. For the second stage of this process, carbon monoxide and water are the feedstock and carbon dioxide and hydrogen are the products.

In additional embodiments, the dry reforming process takes place in the annulus where there is $CO_2$ and $CH_4$ in the oil stream. In this embodiment, the catalyst coats the tubing on the outside and the particular catalyst used is a dry reforming catalyst. This approach solves the basic problem of carbon formation with dry reforming. In conventional settings, the carbon plugs the reactor in a few hours and makes the process impractical. In the apparatus disclosed herein, the crude oil washes the carbon from the catalyst and allows the process to continue.

Once the reformed hydrogen and carbon monoxide are recovered they are pumped down the interior of tubing where they are hydrogenated. In an alternate embodiment, the method and the apparatus may incorporate a catalyst in part of the tubing that makes solvents, and these newly formed solvents may aid in cleaning the outside of the tubing.

In some embodiments, it is most practical to coat both the inside and outside of the tubing in the gas lift apparatus. For example, the gas lift apparatus could be adapted to breakdown the heavier oils in the annulus by thermal cracking. In this example, a catalyst coated on the outside on the tubing may facilitate this process especially when the tubing is heated using the heat from the internal exothermic catalytic process occurring on the interior of the tubing.

There are a number of advantages to using the apparatus and methods described herein. For example, the apparatus and method is carried out using a small footprint because the process is carried out in a linear arrangement. Due to the linear arrangement of the apparatus, it is possible to carry out the process in multiple stages where the catalyst is segregated along the tubing in multiple stages. Another advantage is that this apparatus and method removes the need for a heat exchanger. One of the most important advantages is that the process does not have to deliver a precise product, almost any liquid hydrocarbon will suffice because all of the products are combined and mixed with the crude unrefined product. As mentioned above, another advantage is that the catalyst can be easily changed. Furthermore, the method and apparatus can be conducted under high pressure. Also, the method and apparatus can be used as a hydrate mitigation system and eliminate costly insulation for marine risers.

The processes of the present disclosure may be carried out using the method(s) and apparatus described herein. These methods can be further modified and optimized using the principles and techniques of chemical engineering, mechanical engineering, petroleum chemistry, organic chemistry and/or polymer chemistry as applied by a person skilled in the art. Such principles and techniques are taught, for example, in Lawrie Lloyd's Handbook of Industrial Catalyst (Springer 2011), which is incorporated herein by reference in its entirety.

As an example of the gas lift apparatus being modified to carry out an alternative process, ethene may be converted to ethanol. In general, when there are other gases (other than synthetic gas) being injected into the tubing, these other gasses may be converted to other valuable products. For example, an ethene component in the gas stream may be converted to ethanol by passing ethene over a catalyst either packed in the tubing or through a tubing having a catalyst coated wall.

As an alternate example, the tubing may be coated, either on the outside or on the inside, with a water shift catalyst which would be used to convert $CO_2$ in the production stream to CO and $H_2O$.

In some examples, it may be necessary to control the rate at which the feedstock is converted to the desired product. The conversion rate may be controlled by varying the concentration of the catalyst distributed along the tubing. For example, the catalyst composition along the tubing may be segregated so that different heavy components of the gas stream (C2-C6) are converted into liquids at different points along the tubing. This segregation may allow for better control of the conversion rate as well as better control of the products obtained. These more defined products can then be mixed with crude oil. The same is true for converting any feedstock or gas stream constituents into the desired materials.

An additional advantage of segregating the catalyst in the tubing is that the same tubing can be used for multi-stage conversions. For example, the tubing can be segregated into two or more sections. In the first section, a first catalyst type may be used for a particular conversion. In the second section, a second catalyst type may use the product of the conversion taking place in the first section as a feedstock for a second type of conversion. The use of this type of tandem conversion within the same tubing is extremely beneficial and useful in reducing the industrial footprint needed to carry out this type of operation.

Furthermore, the apparatus disclosed herein is very efficient in that it is configured such that the heat/energy produced due to exothermic nature of the catalytic conversion may be used to inhibit or facilitate other processes. For example, the use of a tubing coated with a catalyst or a tubing packed catalyst where the catalyst undergoes an exothermic reaction allows for the energy produced from this exothermic reaction to be used to inhibit hydrate formation in the annulus where production is flowing (oil gas or both).

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

This example, provides an exemplary method for producing synthetic hydrocarbons. Any and all of the selected method embodiments disclosed herein may be adapted such that any disclosed apparatus may be used to carry out any and all of the disclosed the method embodiments.

In some embodiments, the method for producing synthetic hydrocarbons comprises the steps of: (1) injecting hydrogen and carbon monoxide into a gas lift apparatus; and, (2) forcing synthetic hydrocarbons out of the gas lift apparatus. Also, this method is adapted such that the gas lift apparatus comprises a tubing and an annulus, the tubing is packed with a Fischer-Tropsch catalyst, and the tubing is configured such that hydrogen and carbon monoxide travel past the Fischer-Tropsch catalyst to form synthetic hydrocarbons.

In additional embodiments, the apparatus is configured such that the synthetic hydrocarbons and water flow out of the bottom of the tubing and travel up the annulus to the surface.

In further embodiments, the method may include the following additional steps: (1) separating any hydrogen or carbon dioxide from the synthetic hydrocarbons forced out of the gas lift apparatus; and, (2) reprocessing and re-injecting any hydrogen or carbon dioxide not converted to synthetic hydrocarbons.

In specific embodiments, the method for producing synthetic hydrocarbons is carried out in a producing well. In this embodiment, the method may be modified such that production from the producing well flows up the annulus and cools the synthetic hydrocarbons.

In alternate embodiments, the method for producing synthetic hydrocarbons is carried out in a producing riser. In this embodiment, the method may be modified such that production from the producing riser flows up the annulus and cools the synthetic hydrocarbons.

In additional and/or alternate embodiments, the method for producing synthetic hydrocarbons is carried out in a non-flowing well.

In each of the aforementioned embodiments, the method may be modified by including the following additional steps: (1) circulating cooling fluid up the annulus wherein the cooling fluid mixes with the newly formed synthetic hydrocarbons; (2) separating the cooling fluid from the newly formed synthetic hydrocarbons wherein the separating step takes place at the surface; (3) re-cooling the cooling fluid; and, (4) re-injecting the re-cooled cooling fluid.

Figure 1:
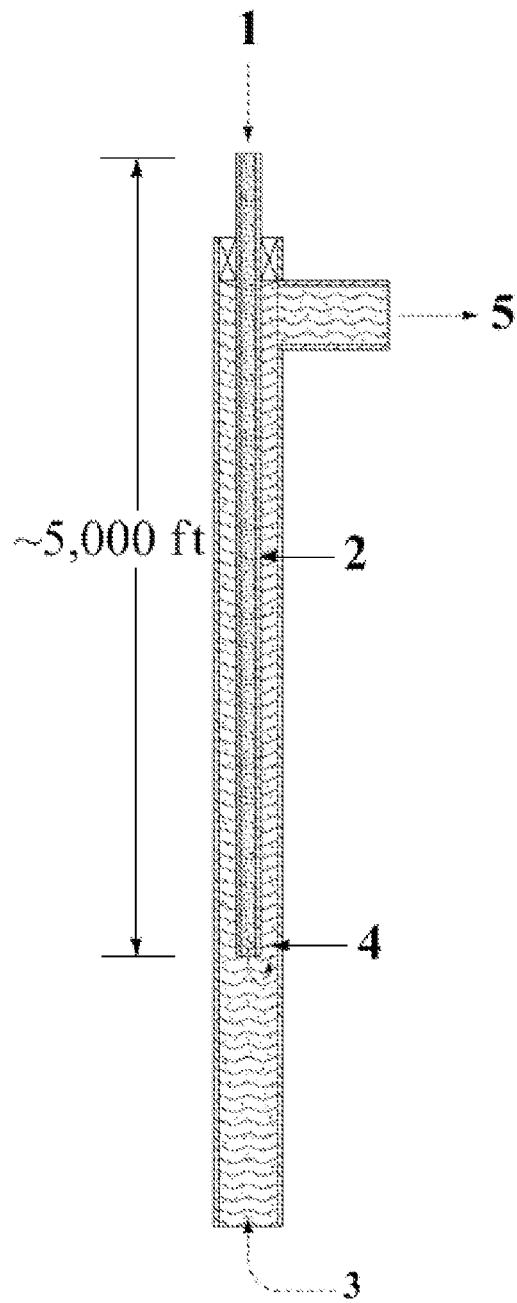
FIG. 1 shows a Fischer-Tropsch Process in a marine riser.

FIG. 1 shows a low temperature high pressure Fischer-Tropsch Process in a producing well. As shown in FIG. 1, the feedstock 1, CO and $H_2$, is injected at 2500 psi. As the CO and $H_2$ travel down a cobalt packed two inch tubing 2, oil, gas and water (250° F.) are pushed out-up through the annulus 4. FIG. 1 provides an example of how synthesis gas is produced and mixed with production 5. The well is producing 12,000 BBLD of oil 3 at 12 mmscfd, 200° F., 1,800 psi and is a mixture of oil, methane and water. As shown in FIG. 1, the tubing containing the catalyst is approximately 5000 feet long.

Figure 2:
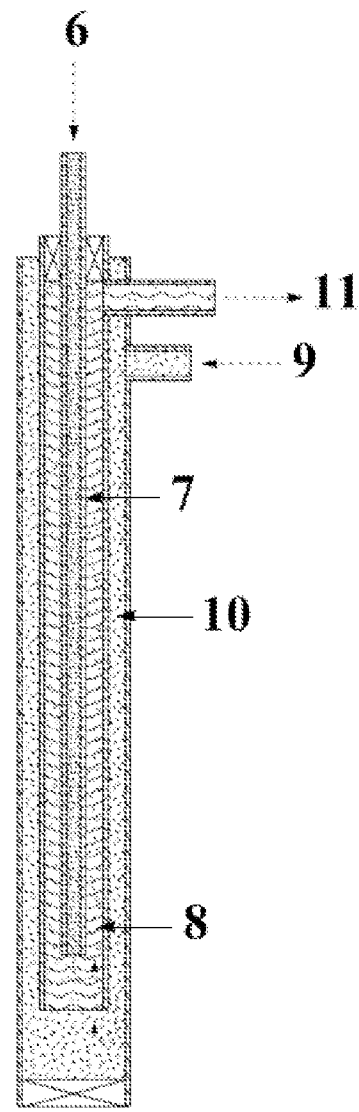
FIG. 2 shows a Fischer Tropsch Process in a dummy well.

FIG. 2 shows a Fischer-Tropsch Process in a dummy well. As shown in FIG. 2, the feedstock 6, CO and $H_2$, is injected at 2500 to 3000 psi at a rate of 1.2 mmscfd. As the CO and $H_2$ flow down a cobalt packed two inch tubing 7, synthetic oil, hot oil and water (205° F.) are pushed out of the annulus 11. Also in FIG. 2, cooling oil 9 is circulated through the cooling casing 10 and mixed with the synthetic hydrocarbon products in the annulus 8 and flow up the annulus and out of the annulus 11 at a rate of 90 gallons per minute (gpm) and at a temperature of 60° F.

Example 2

This example, provides an exemplary apparatus for producing synthetic hydrocarbons. Any and all of the selected apparatus embodiments disclosed herein may be adapted such that the disclosed method(s) may be carried out using any and all of the disclosed the apparatus embodiments.

An apparatus for producing synthetic hydrocarbons comprises at least a tubing and an annulus. For example, the apparatus for producing synthetic hydrocarbons comprises a tubing packed with a Fischer-Tropsch catalyst. The tubing is configured such that as hydrogen and carbon monoxide are injected into the top of the tubing, hydrogen and carbon monoxide travel past the Fischer-Tropsch catalyst to produce synthetic hydrocarbons; and as synthetic hydrocarbons are produced heat is rejected.

In some embodiments, the apparatus may be modified such that the tubing is configured to direct synthetic hydrocarbons and water out of the bottom of the tubing and up the annulus to the surface.

In additional embodiments, the apparatus is modified such that any hydrogen or carbon monoxide not converted to synthetic hydrocarbons travels up the annulus to the surface where the non-converted hydrogen or carbon monoxide is reprocessed and re-injected.

In some embodiments, the apparatus is placed in a producing well. In these embodiments, production from the producing well flows up the annulus and cools the synthetic hydrocarbons.

In additional and/or alternate embodiments, the apparatus is placed in a producing riser. In these embodiments, production from the producing riser flows up the annulus and cools the synthetic hydrocarbons.

In additional and/or alternate embodiments, the apparatus is placed in a non-flowing well. In these embodiments and any of the aforementioned embodiments in Example 3, the apparatus is capable of circulating cooling water up the annulus where it mixes with the newly formed petroleum product, and at the surface, the water is separated and cooled for re-injection.

Example 3

In some embodiments, a method for producing synthetic hydrocarbon derived products comprises the steps of: (1) injecting a feedstock into a gas lift apparatus; and (2) forcing synthetic hydrocarbon derived product out of the gas lift apparatus. The gas lift apparatus comprises a tubing and an annulus, and the tubing further comprises a catalyst. Also, the tubing is configured such that the feedstock travels past the catalyst to form synthetic hydrocarbon derived products.

In specific embodiments, the tubing is coated and/or packed with a catalyst and/or the apparatus is configured such that the synthetic hydrocarbon derived products flow out of the bottom of the tubing and travel up the annulus to the surface.

In some embodiments the method further comprises the steps of: (1) separating any remaining feedstock from the synthetic hydrocarbon products forced out of the gas lift apparatus; and, (2) reprocessing and re-injecting any feedstock not converted to synthetic hydrocarbon products.

In specific embodiments of the method, the feedstock and catalyst are suitable for performing a process selected from the group consisting of the Haber process, the Haber-Bosch process, processes used to industrially produce ammonia or synthesis gas, the Claus process, the gas desulfurizing process, processes used to recover elemental sulfur from gaseous hydrogen sulfide, the Bergius Process, processes used to produce liquid hydrocarbons for use as synthetic fuel by hydrogenation of high-volatile bituminous coal at high temperature and pressure, the Deacon process, the Deacon-Leblanc process, the Sabatier process, the Sabatier-Senderens process, hydrogenation processes, oxidation processes, ammonia oxidation processes, the Andrussov synthesis, hydrocracking processes, alkylation processes, hydrotreating processes, catalytic reforming processes, coke formation, naphtha reforming processes, processes for the formation, reformation and functionaliztion of aromatics, cyclar processes, M2-forming process, catalytic dewaxing processes, isomerization processes, isopropyl alcohol formation, acetone formation, bisphenol-A formation, cumene formation, vinyl chloride formation, oxychlorination processes, formation of synthetic rubber from butadiene and styrene, formation of butadiene from butane or butenes, styrene production, nylon production, production of nylon intermediates, formation of adipic acid, formation of hexamethylenediamine, formation of nylon polymer, the Snia-Viscosa process, hydroformylation and carbonylation processes, metathesis of olefins, the Shell Higher-Olefins process, polyethylene formation, polypropylene formation, formation of ammonia synthesis gas, feedstock purification processes, hydrodesulfurization processes, processes for chlorine removal, sulfur adsorption, steam reforming, carbon monoxide removal, carbon monoxide conversion, and methanation, formation of methanol synthesis gas, formation of OXO synthesis gas, hydrogen production, processes for steam reforming of reducing gas, town gas production, autothermal reforming processes, the Claude Process, processes for volatile organic compound removal, the Fischer-Tropsch process, dry carbon dioxide ($CO_2$) reforming, hydrocarbon cracking of hydrocarbons, and steam reforming.

In more specific embodiments of the method, the feedstock and the catalyst are suitable for performing a process selected from the group consisting of the Fischer-Tropsch process, dry carbon dioxide ($CO_2$) reforming, hydrocarbon cracking of hydrocarbons, and steam reforming.

In some embodiments, the method is carried out in a producing well. Also, the production from the producing well flows up the annulus and cools the synthetic hydrocarbon derived products.

In additional embodiments, the method is carried out in a producing riser. Also, the production from the producing riser flows up the annulus and cools the synthetic hydrocarbon derived products.

In alternate embodiments, the method is carried out in a non-flowing well.

In further embodiments, the method the further comprises the steps of: (1) circulating cooling fluid up the annulus wherein the cooling fluid mixes with the newly formed synthetic hydrocarbon derived products; (2) separating the cooling fluid from the newly formed synthetic hydrocarbon derived products wherein the separating step takes place at the surface; (3) re-cooling the cooling fluid; and, (4) re-injecting the re-cooled cooling fluid.

Example 4

In some embodiments, the apparatus for producing synthetic hydrocarbon derived products comprises (1) a tubing, and (2) an annulus. The tubing is packed or coated with a catalyst. Also, the tubing is configured such that (1) a feedstock is injected into the top of the tubing, (2) the feedstock travels past the catalyst to produce a synthetic hydrocarbon derived product; and, (3) heat is rejected as the synthetic hydrocarbon derived product is produced.

In particular embodiments, the tubing is configured such that the synthetic hydrocarbon derived product and water flow out of the bottom of the tubing and travel up the annulus to the surface.

In some examples, any feedstock not converted to a synthetic hydrocarbon derived product travels up the annulus to the surface where the non-converted feedstock is reprocessed and re-injected.

In particular examples, the feedstock and the catalyst are suitable for producing a hydrocarbon derived product resulting from a process selected from the group consisting of the Haber process, the Haber-Bosch process, processes used to industrially produce ammonia or synthesis gas, the Claus process, the gas desulfurizing process, processes used to recover elemental sulfur from gaseous hydrogen sulfide, the Bergius Process, processes used to produce liquid hydrocarbons for use as synthetic fuel by hydrogenation of high-volatile bituminous coal at high temperature and pressure, the Deacon process, the Deacon-Leblanc process, the Sabatier process, the Sabatier-Senderens process, hydrogenation processes, oxidation processes, ammonia oxidation processes, the Andrussov synthesis, hydrocracking processes, alkylation processes, hydrotreating processes, catalytic reforming processes, coke formation, naphtha reforming processes, processes for the formation, reformation and functionaliztion of aromatics, cyclar processes, M2-forming process, catalytic dewaxing processes, isomerization processes, isopropyl alcohol formation, acetone formation, bisphenol-A formation, cumene formation, vinyl chloride formation, oxychlorination processes, formation of synthetic rubber from butadiene and styrene, formation of butadiene from butane or butenes, styrene production, nylon production, production of nylon intermediates, formation of adipic acid, formation of hexamethylenediamine, formation of nylon polymer, the Snia-Viscosa process, hydroformylation and carbonylation processes, metathesis of olefins, the Shell Higher-Olefins process, polyethylene formation, polypropylene formation, formation of ammonia synthesis gas, feedstock purification processes, hydrodesulfurization processes, processes for chlorine removal, sulfur adsorption, steam reforming, carbon monoxide removal, carbon monoxide conversion, and methanation, formation of methanol synthesis gas, formation of OXO synthesis gas, hydrogen production, processes for steam reforming of reducing gas, town gas production, autothermal reforming processes, the Claude Process, processes for volatile organic compound removal, the Fischer-Tropsch process, dry carbon dioxide (CO2) reforming, hydrocarbon cracking of hydrocarbons, and steam reforming.

In specific embodiments, the feedstock and the catalyst are suitable for producing a hydrocarbon derived product resulting from a process selected from the group consisting of the Fischer-Tropsch process, dry carbon dioxide (CO2) reforming, hydrocarbon cracking, and steam reforming.

In some examples, the apparatus is placed in a producing well. Also, production from the producing well flows up the annulus and cools the synthetic hydrocarbons.

In other examples, the apparatus is placed in a producing riser. The production from the producing riser flows up the annulus and cools the synthetic hydrocarbons.

In alternate examples, the apparatus is placed in a non-flowing well. Also, the apparatus is capable of circulating cooling water up the annulus where it mixes with the newly formed petroleum product, and at the surface, the water is separated and cooled for re-injection.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Patents

U.S. Pat. No. 4,039,302
U.S. Pat. No. 4,826,800
U.S. Pat. No. 5,345,005
U.S. Pat. No. 5,811,365
U.S. Pat. No. 5,945,458

Publications

EP 127220
EP 142887
EP 221598
EP 261870
GB 2125062
GB 2130113
GB 2146350

WO 01/38269
WO 03/090925

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for producing synthetic hydrocarbons comprising:
    a marine riser, wherein the marine riser is suspended in a body of water;
    a tube configured to insert into the top of the marine riser, wherein a Fischer-Tropsch catalyst is comprised inside the tube, and wherein the top of the tube is configured to receive hydrogen and carbon monoxide such that contact of the hydrogen and carbon monoxide with the Fischer-Tropsch catalyst produces synthetic hydrocarbons; and
    an annulus configured to receive the produced synthetic hydrocarbons,
    wherein heat generated by contact of the hydrogen and carbon monoxide with the Fischer-Tropsch catalyst is rejected into the body of water during production of the synthetic hydrocarbons from the annulus.

2. The apparatus of claim 1, wherein the annulus is between an outside wall of the tube and an inside wall of the riser, and wherein the tube is configured such that synthetic hydrocarbons and water generated during contacting flow out of the bottom of the tube and travel up the annulus to the surface.

3. The apparatus of claim 1, wherein any unreacted hydrogen or carbon monoxide travels up the annulus to the surface where the unreacted hydrogen carbon monoxide, or both is reprocessed and re-injected into the top of the tubing.

4. The apparatus of claim 1, wherein the marine riser is a producing well.

5. The apparatus of claim 1, wherein production from the producing well flows up the annulus and cools the synthetic hydrocarbons.

6. The apparatus of claim 1, wherein the apparatus is placed in a non-flowing well.

7. The apparatus of claim 6, further comprising another tube positioned around the tube, wherein the apparatus is capable of circulating cooling fluid up an annulus between the another tube and the inside wall of the riser, where the cooling fluid mixes with the synthetic hydrocarbons, and at the surface, the cooling fluid is separated and cooled for re-injection.

8. An apparatus for producing synthetic hydrocarbon derived products comprising;
    a marine riser, wherein the marine riser is suspended in a body of water;
    a tube configured to insert into the top of the marine riser, wherein one or more catalysts are comprised inside the tube, and wherein the top of the tube is configured to receive feedstock such that contact of the feedstock with at least one of catalysts produces synthetic products; and
    an annulus configured to receive the produced synthetic products, tubing;
    wherein heat generated by contact of the catalyst is rejected into the body of water during production of the synthetic products from the annulus.

9. The apparatus of claim 8, wherein the annulus is between an outside wall of the tube and an inside wall of the riser, and wherein the tube is configured such that the synthetic hydrocarbons and water generated during production of the synthetic products flow out of the bottom of the tube and travel up the annulus to the surface.

10. The apparatus of claim 8, wherein any feedstock not converted to the synthetic products travels up annulus to the surface where the non-converted feedstock is reprocessed and re-injected.

11. The apparatus of claim 8, wherein the feedstock and the catalyst are suitable for producing the synthetic products from a process selected from the group consisting of the Haber process, the Haber-Bosch process, processes used to industrially produce ammonia or synthesis gas, the Claus process, the gas desulfurizing process, processes used to recover elemental sulfur from gaseous hydrogen sulfide, the Bergius Process, processes used to produce liquid hydrocarbons for use as synthetic fuel by hydrogenation of high-volatile bituminous coal at high temperature and pressure, the Deacon process, the Deacon-Leblanc process, the Sabatier process, the Sabatier-Senderens process, hydrogenation processes, oxidation processes, ammonia oxidation processes, the Andrussov synthesis, hydrocracking processes, alkylation processes, hydrotreating processes, catalytic reforming processes, coke formation, naphtha reforming processes, processes for the formation, reformation and functionalization of aromatics, cyclar processes, M2-forming process, catalytic dewaxing processes, isomerization processes, isopropyl alcohol formation, acetone formation, bisphenol-A formation, cumene formation, vinyl chloride formation, oxychlorination processes, formation of synthetic rubber from butadiene and styrene, formation of butadiene from butane or butenes, styrene production, nylon production, production of nylon intermediates, formation of adipic acid, formation of hexamethylenediamine, formation of nylon polymer, the Snia-Viscosa process, hydroformylation and carbonylation processes, metathesis of olefins, the Shell Higher-Olefins process, polyethylene formation, polypropylene formation, formation of ammonia synthesis gas, feedstock purification processes, hydrodesulfurization processes, processes for chlorine removal, sulfur adsorption, steam reforming, carbon monoxide removal, carbon monoxide conversion, and methanation, formation of methanol synthesis gas, formation of OXO synthesis gas, hydrogen production, processes for steam reforming of reducing gas, town gas production, autothermal reforming processes, the Claude Process, processes for volatile organic compound removal, the Fischer-Tropsch process, dry carbon dioxide ($CO_2$) reforming, hydrocarbon cracking of hydrocarbons, and steam reforming.

12. The apparatus of claim 8, wherein the feedstock and the catalyst are suitable for producing a synthetic products from a process selected from a group consisting of the Fischer-Tropsch process, dry carbon dioxide ($CO_2$) reforming, hydrocarbon cracking, and steam reforming.

13. The apparatus of claim 8, wherein the marine riser is a producing well.

14. The apparatus of claim 13, wherein production from the producing well flows up the annulus and cools the synthetic hydrocarbons.

15. The apparatus of claim 8, wherein the marine riser is placed in a non-flowing well.

16. The apparatus of claim 15, further comprising another tube positioned around the tube wherein the apparatus is capable of circulating cooling fluid up an annulus between the another tube and the inside wall of the riser, where the cooling fluid mixes with the synthetic products, and at the surface, the cooling fluid is separated and cooled for re-injection.

17. A system for producing synthetic hydrocarbons comprising:
- a marine riser positioned in a body of water;
- a tube configured to be inserted into the marine riser;
- one or more catalysts capable of being distributed along the inside of the length of the tube;
- a pressurizing unit coupled to the tube, the pressurizing unit capable of pressurizing a feedstock in a downwardly direction through the tube when the tube is inserted in the marine riser, wherein contact of the feedstock with at least one of the catalysts produces a mixture comprising synthetic hydrocarbons; and wherein contacting generates heat, and the generated heat is transferred to the produced mixture in an annulus of the marine riser, and then to the outside wall of the marine riser.

18. The system of claim 17, wherein a length of the tube is sufficient to control the conversion rate or product yield along the length of the tube.

19. The system of claim 17, wherein tube is coiled, and wherein the tube is capable of being uncoiled during insertion of the tube into the marine riser.

20. The apparatus of claim 1, wherein the tube further comprises another catalyst coated on an outside wall of the tube, and wherein contact of the produced synthetic hydrocarbons with the other catalyst to produces additional synthetic hydrocarbons.

21. The apparatus of claim 8, wherein the tube further comprises another catalyst coated on an outside wall of the tube, and wherein contact of the produced synthetic hydrocarbons with the other catalyst to produces additional synthetic hydrocarbons.

* * * * *

UNITED STATES PATENT AND TRADEMARK OFFICE
CERTIFICATE OF CORRECTION

| | | |
|---|---|---|
| PATENT NO. | : 9,005,554 B1 | Page 1 of 1 |
| APPLICATION NO. | : 14/594452 | |
| DATED | : April 14, 2015 | |
| INVENTOR(S) | : Robert P. Herrmann | |

It is certified that error appears in the above-identified patent and that said Letters Patent is hereby corrected as shown below:

On the title page, Item (54) and in the Specification, Column 1, line 2:

In the title, delete "OFFSHORE PRODUCTION RISERS OR OIL" and replace with --OFFSHORE PRODUCTION RISERS FOR OIL -- therefor.

Signed and Sealed this
Eighteenth Day of August, 2015

Michelle K. Lee
*Director of the United States Patent and Trademark Office*